(12) United States Patent
Bossi et al.

(10) Patent No.: US 8,109,160 B2
(45) Date of Patent: Feb. 7, 2012

(54) INSPECTION APPARATUS

(75) Inventors: Richard H. Bossi, Renton, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 483 days.

(21) Appl. No.: 12/366,932

(22) Filed: Feb. 6, 2009

(65) Prior Publication Data

US 2010/0199766 A1 Aug. 12, 2010

(51) Int. Cl.
*G01N 33/00* (2006.01)
(52) U.S. Cl. .......................... 73/865.8; 73/584
(58) Field of Classification Search ................. 73/865.8, 73/584
See application file for complete search history.

(56) References Cited

U.S. PATENT DOCUMENTS

| | | | |
|---|---|---|---|
| 5,216,819 A * | 6/1993 | Givler | 33/832 |
| 5,710,378 A * | 1/1998 | Dykes et al. | 73/601 |
| 6,220,099 B1 * | 4/2001 | Marti et al. | 73/633 |
| 7,231,826 B2 | 6/2007 | Bossi | |
| 7,320,249 B2 | 1/2008 | Georgeson | |
| 7,328,630 B2 | 2/2008 | Wright | |
| 2008/0307637 A1 | 12/2008 | Fogarty | |

OTHER PUBLICATIONS

Wang, Xuefeng, et al., Development of Air-Coupled Ultrasound Transducers for Nondestructive Evaluation, MEMS 2008, Tucson, AZ, USA, Jan. 13-17, 2008, pp. 932-935.

* cited by examiner

*Primary Examiner* — Hezron E Williams
*Assistant Examiner* — Rodney T Frank
(74) *Attorney, Agent, or Firm* — Klintworth & Rozenblat IP LLC

(57) ABSTRACT

An inspection apparatus may include an arm member, a vacuum pump, a contact member, and at least one probe. The contact member may be connected to the arm member and connected to the vacuum pump for contacting and applying vacuum pressure from the vacuum pump to a workpiece surface being inspected. The at least one probe may be connected to the arm member for emitting signals against the workpiece surface being inspected and for receiving signals from the workpiece surface being inspected.

25 Claims, 3 Drawing Sheets

INSPECTION APPARATUS

BACKGROUND OF THE DISCLOSURE

Complex workpieces often need to be inspected using non-destructive inspection/evaluation apparatus and/or methods. One conventional method is a hand-held inspection of the workpiece. However, this method may have a limited range of inspection. Another conventional method is to inspect a workpiece using a probe on the end of a member. However, it may be difficult and/or time-consuming to place the probe properly against the workpiece for the inspection due to the hard-to-reach area and the necessity of the probe being in proper alignment against the workpiece. Another conventional method is magnetic coupling of a probe against the workpiece. However, this may require access to the backside of the workpiece which may not be accessible.

An apparatus and/or method is needed which may solve one or more problems of one or more of the conventional apparatus and/or methods.

SUMMARY OF THE DISCLOSURE

In one aspect of the disclosure, an inspection apparatus is disclosed. The inspection apparatus may comprise an arm member, a vacuum pump, a contact member, and at least one probe. The vacuum pump may be adapted to supply vacuum pressure. The contact member may be connected to the arm member and connected to the vacuum pump for contacting and applying vacuum pressure from the vacuum pump to a workpiece surface being inspected. The at least one probe may be connected to the arm member for emitting signals against the workpiece surface being inspected and for receiving signals from the workpiece surface being inspected.

In another aspect of the disclosure, a method is disclosed of inspecting a workpiece surface. In one step, an inspection apparatus may be provided comprising an arm member, a vacuum pump, a contact member connected to the arm member and to the vacuum pump, and at least one probe connected to the arm member. In another step, the arm member may be used to contact the contact member against the workpiece surface. In an additional step, vacuum pressure may be supplied, using the vacuum pump, to the contact member against the workpiece surface. In another step, signals may be emitted and received, through the at least one probe, against and from the workpiece surface in order to inspect the workpiece surface.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
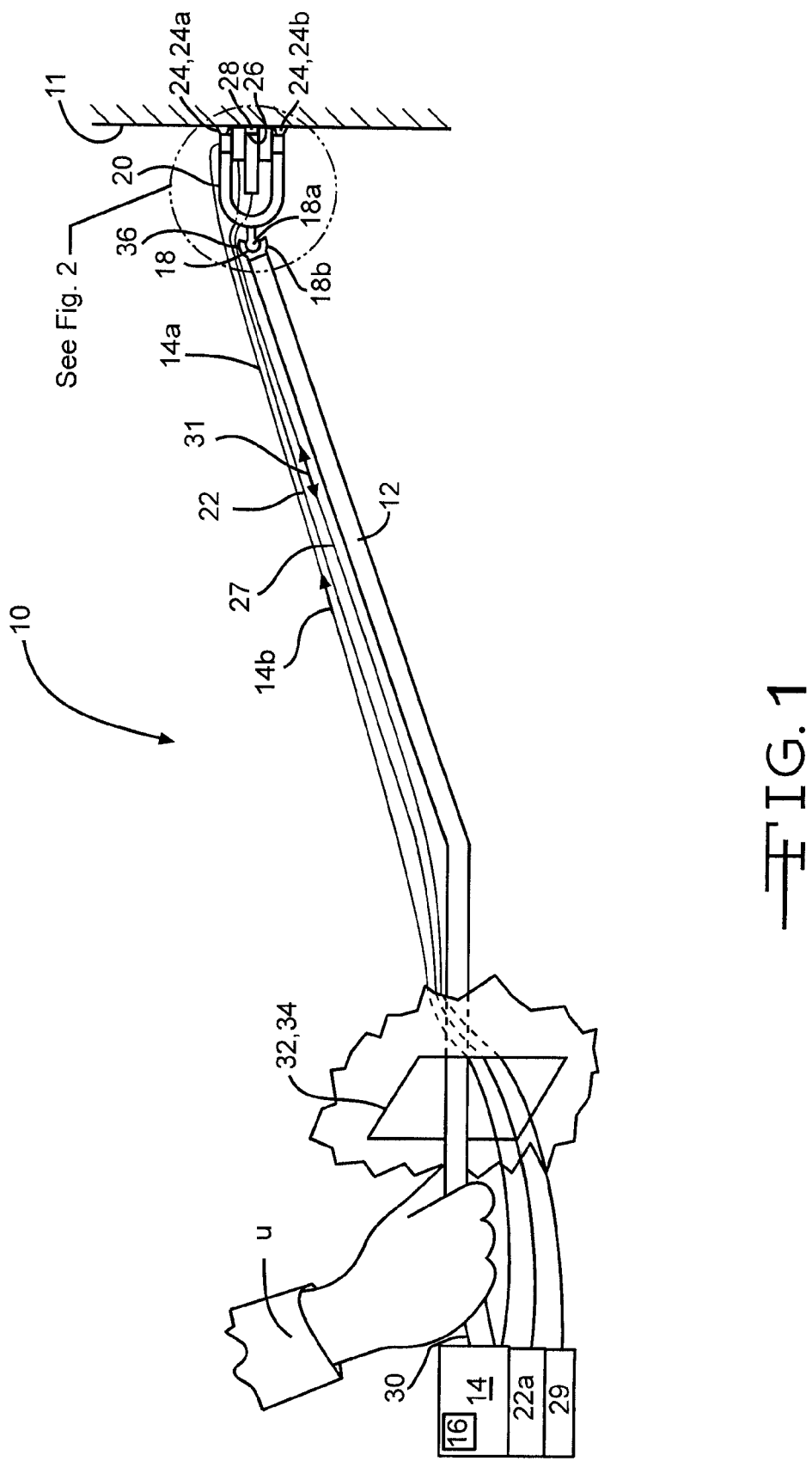
FIG. 1 is a perspective view of an inspection apparatus being used to inspect a workpiece surface.
Figure 2:
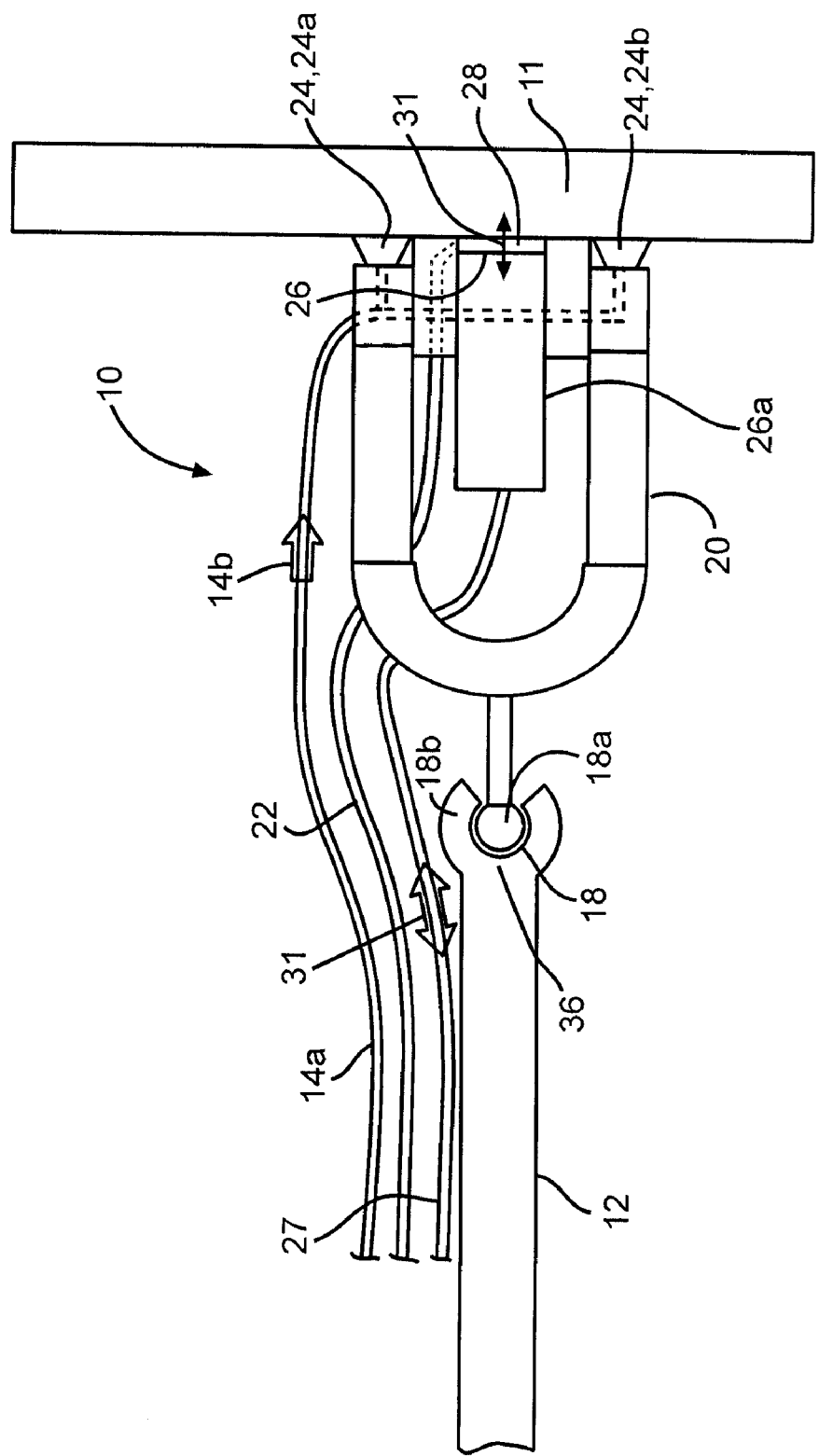
FIG. 2 is a close-up view within the marked circle of the inspection apparatus of FIG. 1.

FIG. 1 is a perspective view of an inspection apparatus 10 being used to inspect a workpiece surface 11. FIG. 2 is a close-up view within the marked circle of the inspection apparatus of FIG. 1. As shown in FIGS. 1 and 2, the inspection apparatus 10 may comprise an arm member 12, a vacuum pump 14, a vacuum line 14a, a control member 16, a joint 18, a housing 20, a couplant line 22, a contact member 24, at least one probe 26, an inspection line 27, and a couplant 28.

The vacuum pump 14 may be connected to an end 30 of the arm member 12. The end 30 of the arm member 12 may be adapted to be gripped by a user U. The control member 16 may comprise a lever, handle, button, or other member on the vacuum pump 14 for turning the vacuum pump 14 on and off. The arm member 12 may fit into and/or through a hard-to-reach area 32 and/or an access hole 34 in order to inspect the workpiece surface 11. The workpiece surface 11 may comprise an airplane surface. In other embodiments, the workpiece surface 11 may vary. The arm member 12 may be non-linear. In other embodiments, the arm member 12 may be in varying configurations. The housing 20 may be rotateably connected to another end 36 of the arm member 12 with the joint 18. The joint 18 may comprise a ball 18a and socket 18b for allowing the housing 20 to rotate relative to the arm member 12.

The housing 20 may be cylindrical. In other embodiments, the configuration of the housing 20 may vary. The contact member 24 may be attached to the housing 20 and thereby be connected to the arm member 12. By rotating the housing 20 relative to the arm member 12, the contact member 24 may be put into proper alignment with the workpiece surface 11 in order to place at least one probe surface 26a of the at least one probe 26 into perpendicular alignment with the workpiece surface 11. The contact member 24 may comprise one or more suction cups 24a and 24b. In other embodiments, the contact member 24 may vary. The vacuum pump 14 may be connected to the contact member 24 with a vacuum line 14a in order to supply vacuum pressure 14b to the contact member 24 to apply suction to the workpiece surface 11 through the contact member 24. When the control member 16 is turned on the vacuum pump 14 may supply vacuum pressure 14b to the contact member 24 and correspondingly to the workpiece surface 11. When the control member 16 is turned off the vacuum pump 14 may release the vacuum pressure 14b from the contact member 24 and correspondingly release the vacuum pressure 14b from the workpiece surface 11.

The at least one probe 26 may be connected to the housing 20 and thereby be connected to the arm member 12. An inspection line 27 may connect the at least one probe 26 to an inspection machine 29 such as an eddy current machine, an ultrasonic machine, and/or another type of inspection machine. The at least one probe 26 may comprise a transducer. The at least one probe 26 may comprise an eddy current transducer, an x-ray transducer, an ultrasonic transducer, and/or another type of probe. In other embodiments, one probe 26 may be utilized as a signal emitter and another probe 26 may be utilized as a signal receiver. Signals 31 may be emitted from the inspection machine 29, through the at least one probe 26, against and/or into the workpiece surface 11, and received by the at least one probe 26. The at least one probe 26 may be disposed so that when the contact member 24 is put into contact or controlled proximity with the workpiece surface 11 and vacuum pressure 14b is applied to the contact member 24, the at least one probe 26 may be put firmly into contact with the workpiece surface 11 with the at least one probe surface 26a in perpendicular alignment relative to workpiece surface 11.

The couplant line 22 may be connected between a couplant supplying device 22a to the at least one probe 26 within the housing 20. The couplant line 22 may comprise a water dribbler line and/or another type of couplant line for supplying/coupling varying types of couplant 28 to the at least one probe 26. The couplant line 22 may supply couplant 28 to the at least one probe 26 in between the at least one probe 26 and the workpiece surface 11. The couplant 28 may comprise a liquid, a solid, a gel, a foam, a rubber, water, and/or another type of couplant. In another embodiment, the couplant 28 may be applied to the at least one probe 26 manually and/or using another device. In still other embodiments, no couplant 28 may be utilized and/or attached to the at least one probe 26.

Figure 3:
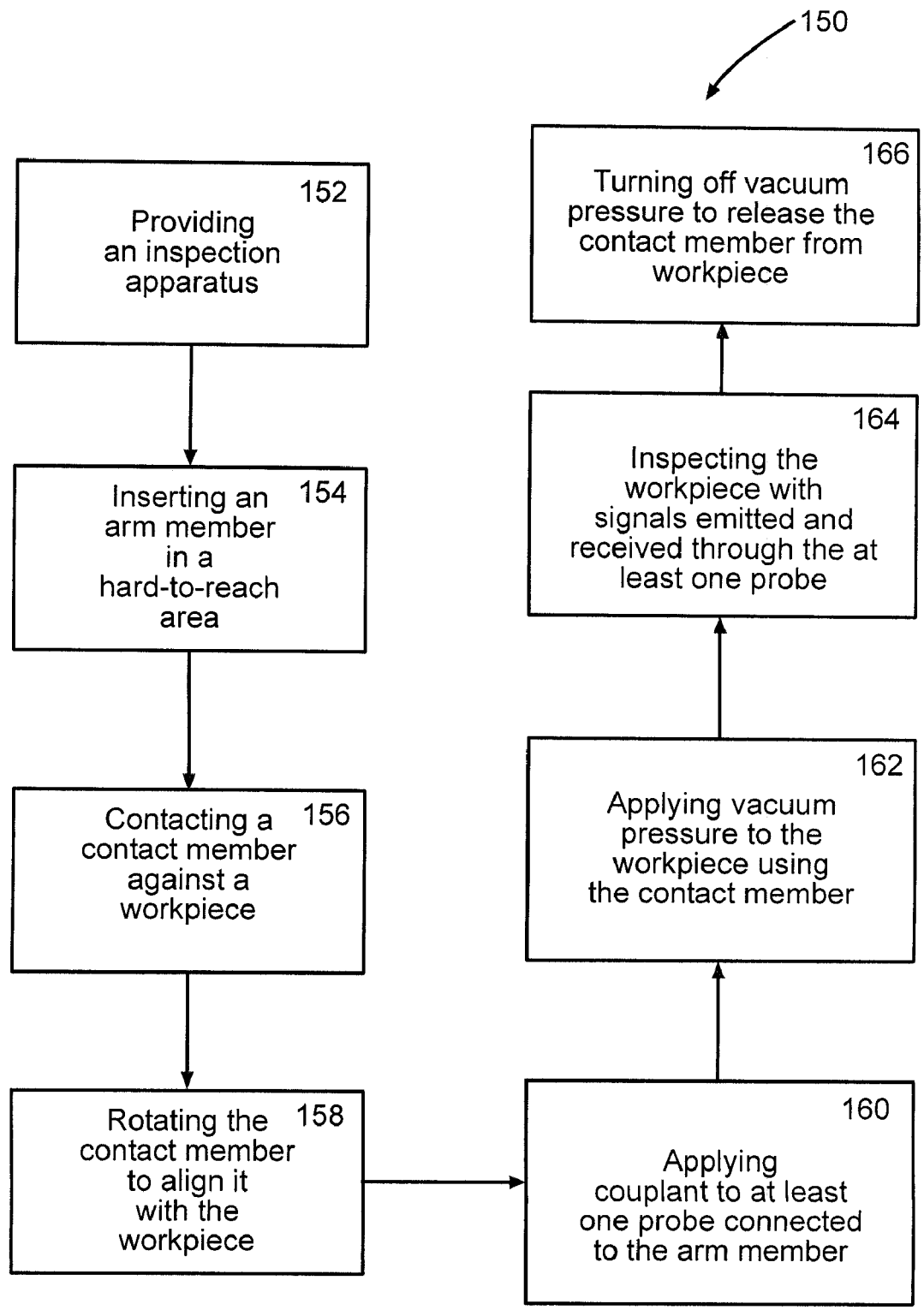
FIG. 3 is a flowchart of one embodiment of a method of inspecting a workpiece surface.

FIG. 3 is a flowchart of one embodiment of a method 150 of inspecting a workpiece surface 11. The workpiece surface 11 may comprise a surface of an airplane or another type of non-airplane surface. In step 152, an inspection apparatus 10 may be provided. The inspection apparatus 10 may comprise an arm member 12, a vacuum pump 14, a contact member 24, and at least one probe 26. The contact member 24 may be connected to the arm member 12 and to the vacuum pump 14. The contact member 24 may comprise one or more suction cups 24a and 24b. In other embodiments, the contact member 24 may comprise varying contact devices for contacting and gripping the workpiece surface 11. The at least one probe 26 may be connected to the arm member 12. The at least one probe 26 may comprise a transducer, an eddy current transducer, an ultrasonic transducer, and/or another type of probe. In other embodiments, one probe 26 may comprise a signal emitter and another probe 26 may comprise a signal receiver. The at least one probe 26 may be attached to an inspection machine 29 such as an eddy current machine, an x-ray machine, an ultrasonic machine, and/or another type of inspection machine. In other embodiments, the inspection apparatus 10 may comprise any of the embodiments disclosed herein.

In step 154, the arm member 12 may be inserted into at least one of an access hole 34 and a hard-to-reach area 32 in order to inspect the workpiece surface 11. In step 156, the arm member 12 may be used to contact the contact member 24 against the workpiece surface 11. In step 158, the contact member 24 may be rotated relative to the arm member 12 in order to align the contact member 24 with the workpiece surface 11. In step 160, a couplant 28 may be applied to the at least one probe 26. The couplant 28 may comprise a liquid, a solid, a gel, a foam, a rubber, water, and/or another type of couplant. In other embodiments, step 160 may occur before step 154. In step 162, vacuum pressure 14b may be supplied, using the vacuum pump 14, to the contact member 24 against the workpiece surface 11. In other embodiments, step 160 may occur after step 162.

In step 164, signals 31 may be emitted from the inspection machine 29, through the at least one probe 26, against and/or into the workpiece surface 11, and back to the at least one probe 26 in order to inspect the workpiece surface 11. The signals 31 may comprise eddy current signals, ultrasonic signals, and/or other types of signals. In step 166, the vacuum pressure 14b may be turned off to release the contact member 24 from the workpiece surface 11. In other embodiments of the method 150, the order of one or more of the steps may be altered, one or more of the steps may be modified, one or more of the steps may not be followed, and/or one or more additional steps may be added.

One or more embodiments of the disclosure may reduce or eliminate one or more problems of one or more of the conventional inspection apparatus and/or methods. One or more embodiments of the disclosure may allow for a hard-to-reach workpiece to be inspected easily, efficiently, quickly, reliably, and/or at low cost.

It should be understood, of course, that the foregoing relates to exemplary embodiments of the disclosure and that modifications may be made without departing from the spirit and scope of the disclosure as set forth in the following claims.

We claim:

1. A hand-held inspection apparatus comprising:
    an arm member comprising a grip configured for a user to hand-hold the inspection apparatus while it is being used to inspect a workpiece surface;
    a vacuum pump for supplying vacuum pressure;
    a contact member connected to the arm member and connected to the vacuum pump for contacting and applying vacuum pressure from the vacuum pump to the workpiece surface being inspected; and
    at least one probe connected to the arm member for emitting signals against the workpiece surface being inspected and for receiving signals from the workpiece surface being inspected.

2. The hand-held inspection apparatus of claim 1 wherein the arm member comprises a first end connected to the vacuum pump and a second end connected to the contact member and the at least one probe.

3. The hand-held inspection apparatus of claim 1 wherein the arm member is sized to fit into at least one of an access hole or a hard-to-reach area.

4. The hand-held inspection apparatus of claim 1 wherein the arm member is non-linear.

5. The hand-held inspection apparatus of claim 1 wherein a housing is rotateably connected to an end of the arm member, and the contact member and the at least one probe are connected to the housing.

6. The hand-held inspection apparatus of claim 5 wherein the housing is rotateably connected to the end of the arm member with a ball and socket.

7. The hand-held inspection apparatus of claim 1 wherein the contact member comprises at least one suction cup.

8. The hand-held inspection apparatus of claim 1 wherein the at least one probe comprises a transducer.

9. The hand-held inspection apparatus of claim 1 wherein the at least one probe is coupled to a couplant comprising at least one of a liquid couplant or a solid couplant.

10. The hand-held inspection apparatus of claim 9 further comprising a liquid dribbler line for supplying the liquid couplant to the at least one probe.

11. The hand-held inspection apparatus of claim 1 further comprising a control member connected to the vacuum pump for turning on the vacuum pump to apply vacuum pressure to a workpiece and for turning off the vacuum pump to release vacuum pressure from a workpiece.

12. The hand-held inspection apparatus of claim 1 wherein the contact member is directly attached to a housing, and the at least one probe is disposed within the housing.

13. The hand-held inspection apparatus of claim 12 wherein the housing is directly attached to the arm member.

14. The hand-held inspection apparatus of claim 1 wherein the vacuum pump is directly attached to the arm member, and a control member is directly attached to the vacuum pump for turning the vacuum pump on and off.

15. The hand-held inspection apparatus of claim 1 wherein the contact member and the at least one probe are only connected to one arm member.

16. The hand-held inspection apparatus of claim 1 wherein the at least one probe is constrained from moving relative to the workpiece surface when the vacuum pump is supplying vacuum pressure to the workpiece surface.

17. The hand-held inspection apparatus of claim 1 wherein an end of the arm member comprises the grip.

18. A method of inspecting a workpiece surface comprising:
    providing a hand-held inspection apparatus comprising an arm member comprising a grip configured for a user to hand-hold the inspection apparatus while it is being used to inspect a workpiece surface, a vacuum pump, a contact member connected to the arm member and to the vacuum pump, and at least one probe connected to the arm member;
    hand-gripping the arm member to contact the contact member against the workpiece surface;
    supplying vacuum pressure, using the vacuum pump, to the contact member against the workpiece surface while hand-gripping the arm member; and
    emitting and receiving signals, through the at least one probe, against and from the workpiece surface in order to inspect the workpiece surface while hand-gripping the arm member.

19. The method of claim 18 further comprising the step of inserting the arm member into at least one of an access hole or a hard-to-reach area in order to inspect the workpiece surface.

20. The method of claim 18 further comprising the step of rotating the contact member relative to the arm member in order to align the contact member with the workpiece surface.

21. The method of claim 18 further comprising the step of applying a couplant to the at least one probe.

22. The method of claim 18 wherein the at least one probe comprises a transducer.

23. The method of claim 18 wherein the contact member comprises at least one suction cup.

24. A method of inspecting a workpiece surface comprising:
    providing an inspection apparatus comprising an arm member, a vacuum pump, a contact member connected to the arm member and to the vacuum pump, and at least one probe connected to the arm member;
    using the arm member to contact the contact member against the workpiece surface by inserting the arm member into at least one of an access hole or a hard-to-reach area in order to inspect the workpiece surface;
    supplying vacuum pressure, using the vacuum pump, to the contact member against the workpiece surface; and
    emitting and receiving signals, through the at least one probe, against and from the workpiece surface in order to inspect the workpiece surface.

25. The method of claim 24 wherein the step of using the arm member to contact the contact member against the workpiece surface comprises inserting the arm member into the access hole in order to inspect the workpiece surface.

\* \* \* \* \*